United States Patent
Oppelt et al.

(10) Patent No.: US 6,285,894 B1
(45) Date of Patent: Sep. 4, 2001

(54) METHOD AND DEVICE FOR NON-INVASIVE IN VIVO DETERMINATION OF BLOOD CONSTITUENTS

(75) Inventors: Arnulf Oppelt, Spardorf; Joachim Kestler, Pinzberg, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/381,986

(22) PCT Filed: Mar. 12, 1998

(86) PCT No.: PCT/DE98/00751

§ 371 Date: Sep. 27, 1999

§ 102(e) Date: Sep. 27, 1999

(87) PCT Pub. No.: WO98/43096

PCT Pub. Date: Oct. 1, 1998

(30) Foreign Application Priority Data

Mar. 25, 1997 (DE) ............................................. 197 12 558
Jul. 28, 1997 (DE) ............................................. 197 32 412

(51) Int. Cl.[7] ..................................................... A61B 5/00
(52) U.S. Cl. ........................... 600/322; 600/335; 600/310
(58) Field of Search .................................. 600/309–310, 600/316, 322–324, 326, 334–335

(56) References Cited

U.S. PATENT DOCUMENTS

| | | |
|---|---|---|
| 4,869,261 | 9/1989 | Penáz . |
| 4,927,264 * | 5/1990 | Shiga et al. ............................. 356/41 |
| 5,111,817 * | 5/1992 | Clark et al. ........................... 600/323 |
| 5,183,042 | 2/1993 | Harjunmaa et al. . |
| 5,372,135 | 12/1994 | Mendelson et al. . |
| 5,372,136 | 12/1994 | Steuer et al. . |
| 5,539,207 | 7/1996 | Wong . |
| 5,638,816 * | 6/1997 | Kiani-Azarbayjany et al. .... 600/316 |

FOREIGN PATENT DOCUMENTS

| | | |
|---|---|---|
| 107 982 | 8/1974 | (DE) . |
| 2 262 337 | 6/1993 | (GB) . |
| WO 96/39926 | 12/1996 | (WO) . |

OTHER PUBLICATIONS

"Quantative FT–IR Spectrometry of Blood Constituents," Stohr et al., Conf. Proc. 14th annual Int. Conf. of the IEEE/EMBS, Paris, Oct. 29–Nov. 1, 1992, pp. 173–174.

"Technology for Non–Invasive Monitoring of Glucose," Heise, Conf. Proc. 18th Annual Int. Conf. of the IEEE/EMBS, Amsterdam, Oct. 31–Nov. 3, 1996.

"Photoelectric Determination of Arterial Oxygen Saturation in Man," Wood et al., J. Lab. Clin. Med. 34, 1949, pp. 387–401.

"Heritage of the Tissue–Bed Oximeter," Geddes, IEEE Eng. in Medicine and Biology, Mar./Apr. 1997, pp. 87–91.

* cited by examiner

Primary Examiner—Eric F. Winakur
Assistant Examiner—Matthew Kremer
(74) Attorney, Agent, or Firm—Schiff Hardin & Waite (57) ABSTRACT

The body part under examination has its thickness modulated by mechanical influence with at least two pressure modulation frequencies. At least four measured signals that are dependent both on the influence of the light as well as on the mechanical thickness change are acquired by irradiating the body part with light.

21 Claims, 7 Drawing Sheets

METHOD AND DEVICE FOR NON-INVASIVE IN VIVO DETERMINATION OF BLOOD CONSTITUENTS

BACKGROUND OF THE INVENTION

1. Field of the Invention

The present invention is directed to a method and an apparatus for non-invasive, in vivo determination of blood constituents of the type wherein light absorption in a body part is monitored while the body part is being subjected to an external mechanical influence.

2. Description of the Prior Art

A method and an apparatus of the above general type for determining a blood constituent are disclosed by U.S. Pat. No. 5,372,135. Blood is thereby expressed by external pressure pulses from the tissue to be examined in order to obtain spectra given different blood volumes. Measured values with and without external pressure are subtracted from one another and difference spectra are thereby acquired. Light wavelengths varied by an acousto-optical filter are thereby utilized. The concentration of the blood constituent, specifically of blood glucose, is then determined from the difference spectra. In U.S. Pat. No. 5,372,136, the modification of the transirradiated light intensity by pulsating blood (AC value) and the transirradiated light intensity itself (DC value) are evaluated at two wavelengths at which the constituent (hematocrit) to be identified respectively absorbs. In addition, the absorption of the constituents (water) not to be identified is at least ten times lower then the absorption of the constituent (hematocrit) to be identified. In particular, these wavelengths are isobestial, i.e. the absorption coefficient of oxygenated and de-oxygenated hemoglobin is the same. Both the natural blood pulse as well as an artificial pulsation with the assistance of a stepping motor can be utilized for the AC values. The possibility of utilizing the method for the identification of other blood constituents is referenced without more detailed particulars.

Measuring blood constituents, particularly glucose, non-invasively by the measurement of the absorption of light is known from the references of E. Stohr et al, "Quantitative FT-IR Spectometry of Blood Constituents", conference proceedings 14th Annual International Conference of the IEEE-EMBS, Paris, Oct. 29, through Nov. 1, 1957 and H. M. Heise, "Technology for Non-Invasive Monitoring of Glucose", Conference Proceedings 18th Annual Conference of the IEEE-EMBS, Oct. 31, through Nov. 3, 1996, Amsterdam.

When measuring the concentration of constituents, it is often a complicating factor that the measured quantity is also sensitively dependent on other parameters then the concentration of a constituent. No reproducible signal can then be obtained without constant re-calibration.

This problem particularly occurs when the concentration of blood sugar is to be identified non-invasively in vivo. Specific optical measuring methods are conventionally employed for this purpose, such as rotation of the polarization plane dependent on the concentration, optical or acousto-optical spectroscopy of the infrared bands of the sugar, techniques making use of the Raman effect and techniques making use of light scatter in the tissue which changes with the glucose concentration.

The determination of the glucose concentration by optical spectroscopy is complicated by the superimposition of the absorption bands of water. Attempts are therefore often made to measure the glucose concentration at wavelength pairs that are sought out such that only water absorbs at the one wavelength but water and glucose absorb at the other. True-to-scale subtraction of the absorption signals then yields a signal value proportional to the glucose concentration.

A problem with this known method, however, is that even extremely minute fluctuations of the scaling of factor lead to errors that cannot be compensated.

The idea of initially making the beam path empty of blood with a pressure capsule in order to obtain a defined initial measured value and to then obtaining a further measured value with the blood flowing back in derives from Wood and Geraci (1949). This principle was employed for the optical identification of the blood oxygenation (E. H. Wood and J. E. Geraci, Photoelectric determination of arterial oxygen saturation in man, Journ. Lab. Clin. Med. 34, 387–401 (1949)).

The article by L. A. Geddes, "Heritage of the Tissue-Bed Oximeter", which appeared in IEEE Engineering in Medicine and Biology, March/April 1997, pp. 87–91, provides an overview of various embodiments of measuring devices for the non-evasive determination of blood oxygen concentration.

East German Patent 107 982 discloses a method and an apparatus for the analysis of emitted radiation of pressure-modulated gases for concentration identification. The concentration-dependent emission of light thereby ensues from a flow-through bulb. In the context of this East German patent, emitted radiation is the cell-luminescence of the gas that, for example, is excited by a gas discharge.

British Specification 2 262 337 A is likewise directed to the spectroscopy of gases, whereby the absorption of a reference cell is pressure-modulated with an acoustic resonator.

U.S. Pat. No. 5,539,207 discloses a technique for identifying tissue by infrared spectroscopy with and without pressure by comparing to spectra of a known tissue. No constituents are quantified.

For determining blood constituents, the aforementioned U.S. Pat. No. 5,372,136 discloses that tissue be transirradiated with light of a plurality of wavelengths and that the pulsing blood stream be simulated by a compress operated with a stepping motor.

PCT Application WO 98/43096 discloses how blood glucose can be identified by application of light of a plurality of wavelengths and active induction of a harmonic change of the blood volume, for example with an inflatable balloon or by temperature variation.

SUMMARY OF THE INVENTION

It is an object of the present invention to provide a method and an apparatus for determining blood constituents wherein the aforementioned problems associated with known techniques and devices are avoided.

This object is achieved in accordance with the principles of the present invention in a method and an apparatus wherein, by external mechanical influence, the body part is harmonically modulated in thickness with at least one further pressure modulation frequency; at least four measured signals that are dependent both on the influence of the light as well as on the mechanical change in thickness are acquired; and in that the concentration of the blood constituent is identified from the at least four measured signals. As a result of the modulation, the measurement results are independent of the defined compression (i.e., of the defined amount of blood expressed from the body part being examined).

In the inventive apparatus for non-invasive determination of the concentration of blood constituents, a unit for compressing the body part is provided which is connected to at least two generators which produce respectively different pressure modulation frequencies.

DETAILED DESCRIPTION OF THE PREFERRED EMBODIMENTS

The invention represents a reproducible, self-calibrating method for non-invasive determination of the glucose concentration in vivo with optical spectroscopy that is based on periodic, harmonic thickness modulations of an illuminated body part. It is thereby assumed that light having at least two defined wavelengths $\lambda$ of the input intensity $I_0$ is beamed into the body part under examination and a signal I arises that can be both the light re-emerging from the extremity—whether after transmission or after reflection—as well as an acoustic wave excited by the absorption of the light that has been beamed in.

Biological tissue is composed of various liquid parts of blood, interstitial and intracellular fluid. The glucose required for the energy supply of the cells is transported in by the blood and proceeds into the interstitial and intracellular fluid by diffusion. Due to different permeability of the cell membranes, various glucose concentrations arise in the three fluid parts. The glucose concentration is thereby similar in the blood and in the interstitial fluid, and the glucose concentration in the cells becomes lower because, of course, glucose is burned therein. Only the knowledge of the average glucose concentration, however, is of significance for monitoring persons.

Figure 1:
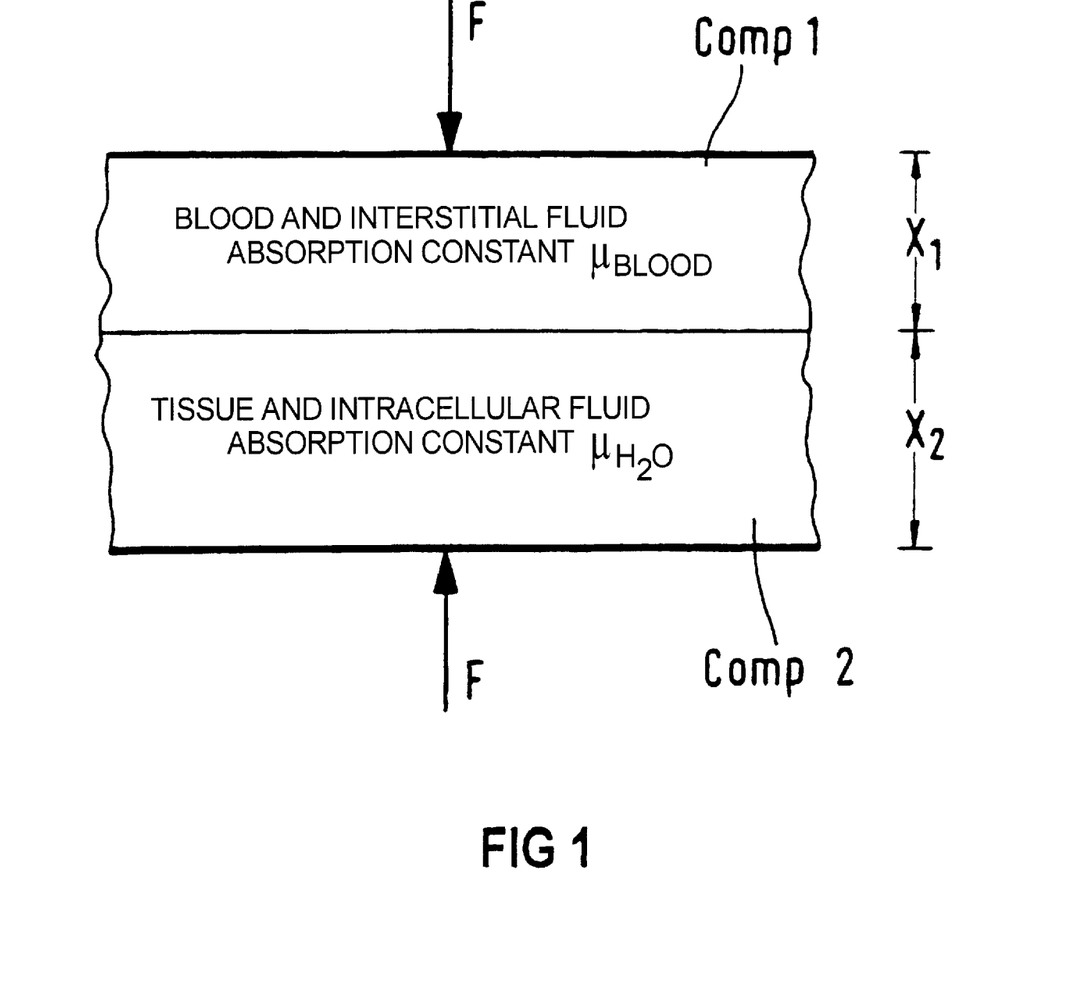
FIG. 1 is a representation of a body part from which a non-invasive in vivo determination of a blood constituent is to be obtained, represented in the form of a model having two basic components for explaining the method and apparatus of the invention.

In order to understand the functioning of the blood constituent measurement, let it therefore be assumed that the transilluminated body part can be described as a two-compartment model composed of blood, interstitial fluid and glucose dissolved therein and of tissue and intracellular fluid with negligible glucose concentration. Thereby let the light absorption in the first compartment Comp1 be determined by the product of the absorption constant of the blood of the interstitial fluid—referenced $\mu_{blood}$ here—and the vessel thickness $x_1$, and by the product of the absorption constant of the tissue and of the intracellular fluid $\mu_{H2O}$ and the tissue thickness $x_2$ in the second compartment Comp2. Such a model is shown in FIG. 1. The arising measured signal derives according to the Beer-Lambert law.

$$I=I_0(\exp(-\mu_{blood}(\lambda)x_1-\mu_{H2O}(\lambda)x_2)=I(\rho),$$

with $$\rho(\lambda)=\mu_{blood}(\lambda)x_1+\mu_{H2O}(\lambda)x_2.$$

Because the light absorption of the blood is essentially additively composed of that of the water in the blood and the glucose dissolved therein $$\mu_{blood}=\mu_{H2O}+\mu_{Glucose}k,$$

whereby the lateral is proportional to the glucose concentration, there follows $$\rho(\lambda)=\mu_{H2O}(\lambda)\cdot(x_1+x_2)+\mu_{Glucose}kx_1.$$

$I_0$: incoming (radiated-in) light intensity
I: emerging light intensity
$\mu_{H2O}$: absorption of tissue water
$\mu_{Glucose}$: absorption of glucose ($<<\mu_{H2O}$)
k: concentration of the glucose.

When the object is squeezed with a force F, the thicknesses change according to Hooke's law $$\frac{\partial x_1}{\partial F}=\varepsilon_1 \text{ and } \frac{\partial x_2}{\partial F}=\varepsilon_2,$$

whereby $\epsilon_1$ and $\epsilon_2$ are the compressibilities of blood vessel and of tissue. Given influence of a force $F=F_0 \cos 2\pi vt$ on the subject under examination that varies harmonically with the frequency v, the light intensity merging from the subject under examination varies according to $$\frac{\partial I}{\partial F} F_0 \cos 2\pi vt.$$

A signal thus is obtained that corresponds to the derivative of the transirradiated intensity at the wavelength $\lambda$. The amplitude of this signal is $$S(\lambda, v) = \frac{\partial I(\lambda)}{\partial F} F_0 = (A+B+C) \cdot F_0$$

whereby $$A = \frac{\partial I(\lambda)}{\partial \rho} \mu_{H2O}(\lambda)\varepsilon_1(v)$$

$$B = \frac{\partial I(\lambda)}{\partial \rho} \mu_{Glucose}(\lambda)k\varepsilon_1(v)$$

$$C = \frac{\partial I(\lambda)}{\partial \rho} \mu_{H2O}(\lambda)\varepsilon_2(v)$$

When the force applied to the extremity is modulated not only with one frequency but with (at least) two, the signal will differ because of the delayed response of the subject under examination to a delta surge at the two modulation frequencies. Given application of two wavelengths $\lambda_1, \lambda_2$, whereof one lies in the range at which no glucose absorption occurs, and of two pressure modulation frequencies $v_1$ and $v_2$, the following measuring situations thus arise:

|  | Modulation Frequency $v_1$ | Modulation Frequency $v_2$ |
|---|---|---|
| Wavelength $\lambda_1$ | $S_1 = a_{11}$ | $S_2 = a_{12}$ |
| Wavelength $\lambda_2$ | $S_3 = a_{21} + b_1 k$ | $S_4 = a_{22} + b_2 k$ | whereby $$a_{11} = \frac{\partial I(\lambda_1)}{\partial \rho} F_0 \mu_{H2O}(\lambda_1)(\varepsilon_1(v_1) + \varepsilon_2(v_1))$$

$$a_{12} = \frac{\partial I(\lambda_1)}{\partial \rho} F_0 \mu_{H2O}(\lambda_1)(\varepsilon_1(v_2) + \varepsilon_2(v_2))$$

$$a_{21} = \frac{\partial I(\lambda_2)}{\partial \rho} F_0 \mu_{H2O}(\lambda_2)(\varepsilon_1(v_1) + \varepsilon_2(v_1))$$

$$a_{22} = \frac{\partial I(\lambda_2)}{\partial \rho} F_0 \mu_{H2O}(\lambda_2)(\varepsilon_1(v_1) + \varepsilon_2(v_2))$$

$$b_1 = \frac{\partial I(\lambda_2)}{\partial \rho} F_0 \mu_{Glucose} \varepsilon_1(v_1)$$

$$b_2 = \frac{\partial I(\lambda_2)}{\partial \rho} F_0 \mu_{Glucose} \varepsilon_1(v_2)$$

$S_{1\ldots 4}$: Measured signals corresponding to the transirradiated light intensity or, respectively, the excited acoustic intensity.

Wherein the electronics is then balanced such that

|  | Modulation Frequency $v_1$ | Modulation Frequency $v_2$ |
|---|---|---|
| Wavelength $\lambda_1$ | $S_1$ | $S_1$ |
| Wavelength $\lambda_2$ | $S_1$ | $S$ | i.e. the second column with $$\frac{S_1}{S_2}$$

and the second row with $$\frac{S_1}{S_3}$$

is multiplied, the following derives for the signal S at the modulation frequency $v_2$ and the wavelength $\lambda_2$ (at which the sugar absorbs)

$$S = \frac{a_{11}}{a_{12}} \frac{a_{11}}{a_{21} + b_1 k}(a_{22} + b_2 k)$$

$$= \frac{a_{11}}{a_{12}} \frac{a_{22}}{a_{21}} \frac{1 + \frac{b_2}{a_{22}} k}{1 + \frac{b_1}{a_{21}} k}$$

$$= \frac{a_{11}}{a_{12}} \frac{a_{22}}{a_{21}}\left(1 + \left(\frac{b_2}{a_{22}} - \frac{b_1}{a_{21}}\right)k\right)$$

Since $$\frac{a_{11}}{a_{12}} \frac{a_{22}}{a_{21}} = 1,$$

$$\Delta S = a_{11}\left(\frac{b_2}{a_{22}} - \frac{b_1}{a_{21}}\right)k$$

$$= \frac{\partial I(\lambda_1)}{\partial \rho} F_0 \frac{\mu_{H2O}(\lambda_1)}{\mu_{H2O}(\lambda_2)} \mu_{Glucose} \varepsilon_1(v_1)\left(\frac{1 + \frac{\varepsilon_2(v_1)}{\varepsilon_1(v_1)}}{1 + \frac{\varepsilon(v_2)}{\varepsilon_1(v_2)}} - 1\right)k = \beta k$$

follows for the signal difference $\Delta S = S_1 - S$.

This expression is proportional to the glucose concentration without additive constants. The constant $\beta$ is identified by an individual, one-time calibration measurement. This can occur, for example, by comparison to the generally introduced finger prick measuring strip.

The case is especially simple when the thickness modulation frequency v is selected so high that the blood in the vessel can no longer follow. This means that $$\varepsilon_1(v_2) \approx 0$$

and then $$\beta = -\frac{\partial I(\lambda_1)}{\partial \rho} F_0 \frac{\mu_{H2O}(\lambda_1)}{\mu_{H2O}(\lambda_2)} \mu_{Glucose} \varepsilon_1(v_1)$$

This factor is in turn determined by comparison to a different method, for example the finger prick method.

One disadvantage of the described method initially seems to be that the proportionality factor $\beta$ is dependent on the relationship of the absorption coefficients $$\frac{\mu(\lambda_1)}{\mu(\lambda_2)}$$

of water. It is known that the absorption coefficient of water is temperature-dependent at certain wavelengths as a consequence of excited OH vibration oscillations. This effect was examined in the publication "Tissue Temperature by Near-Infrared Spectroscopy" by Jeffrey J. Kelly, Katherine A. Kelly and Clyde H. Barlow in SPIE Vol. 2389, pp. 818–828 (1995). It turns out that the absorbency of a 1 mm thick water layer given a wavelength of 1450 nm changes from approximately 1.6 to 1.8 between 17 and 45° C., this corresponding to a relative change of the absorption $$\frac{\Delta \mu}{\mu}$$

by 20%. Steps can be taken, however, to ensure that temperature fluctuations of the tissue and of the blood remain below 2° C. for in vivo measurements. Relative changes of the absorption around 1% are then to be anticipated, so that a calibration error of 2% would derive on the basis of temperature fluctuations. This is entirely adequate for the determination of the glucose concentration.

A further complicating factor may arise because the absorption coefficients $\mu(\lambda_1)$, $\mu(\lambda_2)$ of the water apparently vary over time as a result of other additives in the blood such as cholesterol, albumin or urea; i.e. the calibration factor $\beta$ changes. In this case, it is beneficial to beam light in not only at the two wavelengths $\lambda_1, \lambda_2$ but at even more wavelengths, so that one can recognize from the spectral curve of the absorbency over time whether the water spectrum varies as a consequence of temperature variations or due to other constituents. This can ensue by comparison to calibration spectra that are deposited in a data bank. A correction factor for the relationship $$\frac{\mu(\lambda_1)}{\mu(\lambda_2)}$$

can then be acquired therefrom, this taking a modified water spectrum into consideration.

More than two pressure modulation frequencies can also be applied for further enhancing the precision. Given, for example, employment of four frequencies $v_{1a}, v_{1b}, v_{2a}, v_{2b}$, one thus obtains two independent glucose concentration values from whose deviation one can then draw conclusions above the quality of the measured result; by averaging them, the measuring precision can be enhanced.

The wavelengths with which the glucose concentration is preferably identified lie in the infrared. The range 1.35–1.5 μm is expedient for the referenced wavelength $\lambda_1$ at which the glucose constituent absorbs no light; the range 1.5–1.8 μm is expedient for the measuring wavelength $\lambda_2$ at which glucose absorbs. Laser diodes are preferably utilized as light sources, but light-emitting diodes or thermal light sources in conjunction with a monochromator also may be used; photodiodes may be used as detectors.

A photodetector without preceding wavelength filter cannot distinguish between the light of the two wavelengths $\lambda_1$ and $\lambda_2$. In order to avoid a complicated wavelength filter, the light sources at the two wavelengths are amplitude-modulated with two different frequencies $f_1$ and $f_2$. The modulation frequencies of the light sources are expediently placed in the kilohertz range in which noise-free signal processing is possible and an increasing signal attenuation due to tissue scatter does not yet occur. The output signal of the photo detector is then phase-sensitively respectively rectified with the two intensity modulation frequencies $f_1$ and $f_2$, as a result whereof independent measured signals corresponding to the two wavelengths $\lambda_1$ and $\lambda_2$ are obtained. The ambient light also does not influence the measurement.

The expedient modulation frequencies $v_1$ and $v_2$ for the thickness of the subject under examination depend on the mechanical properties of the body part. The pressure modulation frequencies must be so low that blood can still be expressed out of the examination region and can turn flow back in; however, they should be different from the pulse frequency so that this does not disturb the measurement. The frequency range 1–50 Hz is suitable here. However, there is also the possibility of synchronizing one of the pressure modulation frequencies with the heart beat.

Figure 2A:
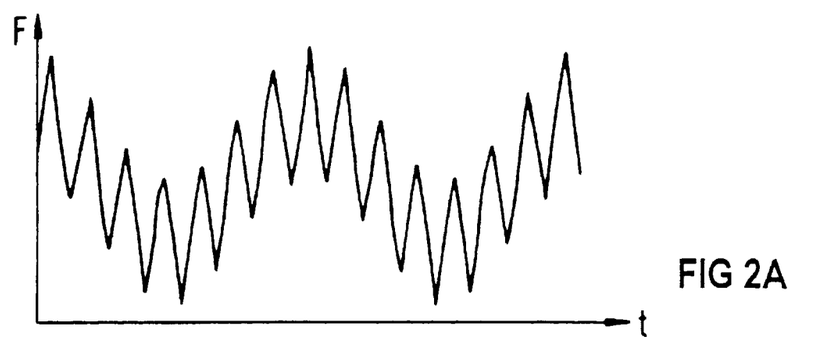
FIGS. 2A, 2B and 2C respectively illustrate the composite time curve produced by two pressure modulation frequencies simultaneously applied to the body part in accordance with the invention, with respective different amplitude relationships.
Figure 2B:
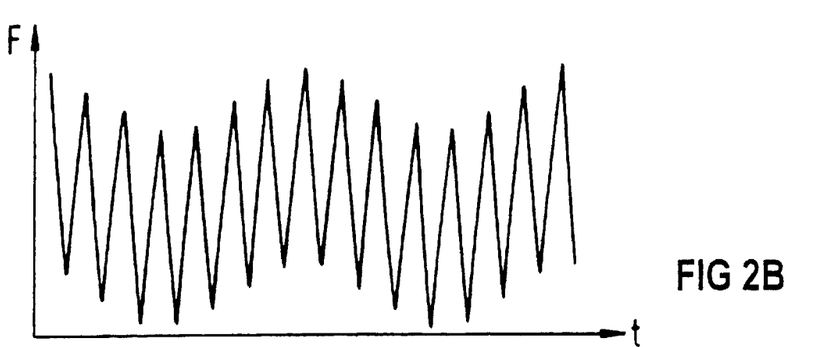
Figure 2C:
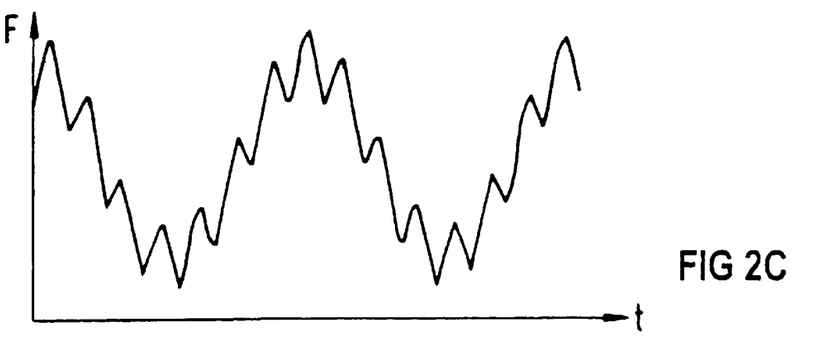

There is also the possibility of selecting the pressure amplitudes differently at the two pressure modulation frequencies $v_1$ and $v_2$ in order to influence the corresponding measured signals in terms of their order of magnitude and adapt them to one another. FIGS. 2A, 2B and 2C show three examples of this: in FIG. 2A, the pressure amplitudes at both pressure modulation frequencies are the same; in FIG. 2B, the pressure amplitude of the higher pressure modulation frequency is greater; in FIG. 2C, it is smaller then that of the lower pressure modulation frequency. In general, the amplitude with the higher frequency will be selected greater then the amplitude with the lower frequency when the body part has a more highly attenuating effect for the higher frequency then for the lower.

Further, it must be assured that the quantity β that derives from the material properties $\epsilon_1(v_1), \epsilon_2(v_1), \epsilon_1(v_2), \epsilon_2(v_2)$ of the examination subject is clearly different from zero. The second pressure modulation frequency should then be set such that the quantity β becomes optimally large but a clear measured signal $S_4$ is nonetheless still observed. This is to be anticipated when the second pressure modulation frequency $v_2$ corresponds to approximately 2 through 3 times the value of the first frequency $v_1$.

In particular, however, the pressure modulation frequency $v_1$ can also be made equal to zero, i.e. the direct signal is used and the pressure modulation frequency $v_2$ is selected such that the blood-filled vessel can no longer follow, i.e. $\epsilon_1 \approx 0$ applies. This is to be anticipated given pressure modulation frequencies of a few tens of Hertz, for example 10 Hz through 30 Hz.

Figure 3:
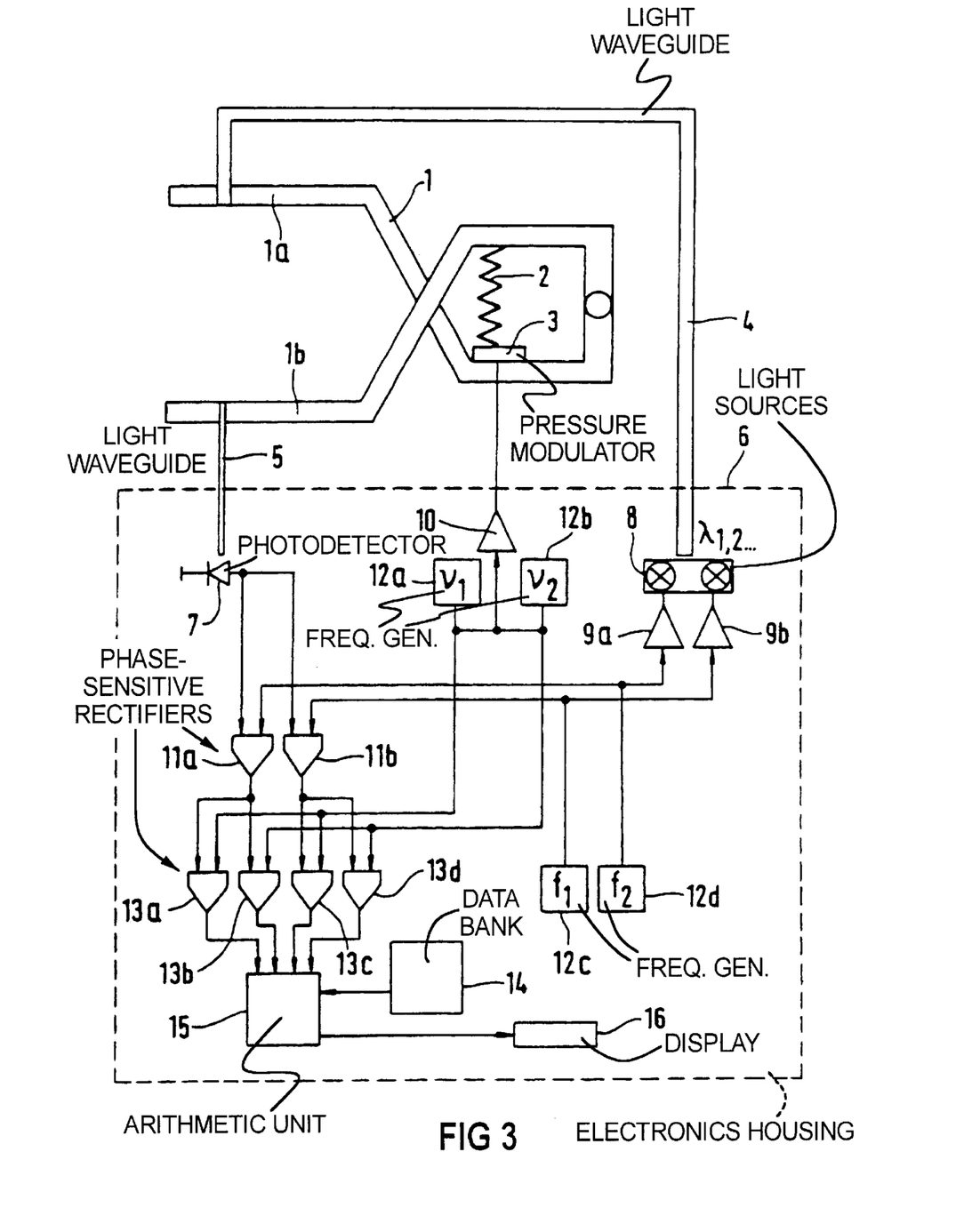
FIG. 3 is a schematic illustration of a first embodiment of a measuring apparatus constructed and operating in accordance with the principles of the present invention.

Exemplary apparatus implementations for the described measuring method are shown in FIGS. 3 through 6:

An applicator 1 in the form of a clamp is applied to a body part, for example the little finger, the ear lobe or the lip. A pressure spring 2 produces reproducible pressing power. Moreover, an actuator in the form of a pressure modulator 3 is attached to the clamp, this generating periodic pressure fluctuations in the body part embraced by the clamp by being driven with a plurality of frequencies $v_1$ and $v_2$. The actuator 3 can be composed of piezoelectric or electromagnetic transducers. In order to reduce thermal influences on the measurement, the pressure jaws 1a, 1b of the applicator 1 can be thermally insulated or tempered. Intensity-modulated wavelengths are applied to the body part via a waveguide 4 and the transirradiated light is carried off via a waveguide 5. Frequency generators 12c, 12d generate the frequencies $f_1$, $f_2$ that, via amplifiers 9a, 9b, are supplied to light sources 8, preferably laser diodes, for intensity modulation. Frequency generators 12a, 12b respectively generate frequencies $v_1$, $v_2$ that are supplied to the pressure modulator 3 via an amplifier 10. The received light is supplied to a photodectector 7 via the waveguide 5, phase-sensitive rectifiers 11a, 11b for the photo dectector signals with the reference frequencies $f_1$, $f_2$ following these as frequency filters for the separation of the frequencies $f_1$, $f_2$ according to the light modulation. The signals acquired in this way are supplied to further phase-sensitive rectifiers 13a–13d with reference frequencies $v_1$, $v_2$ as frequency filters for separating the measured signals according to the thickness modulation. The output signals of the phase-sensitive rectifiers 13a, 13b, 13c, 13d are supplied to an analog or digital arithmetic unit 15 that, taking a data bank 14 with calibration and correction values into consideration, outputs the blood glucose concentration at a display 16. The arithmetic unit 15 also may take different pressure modulation and intensity modulation amplitudes into consideration. By using technologies of microelectronics, the entire signal generating and evaluation circuit can be accommodated in an electronics housing 6 that can be worn by a person.

Figure 4:
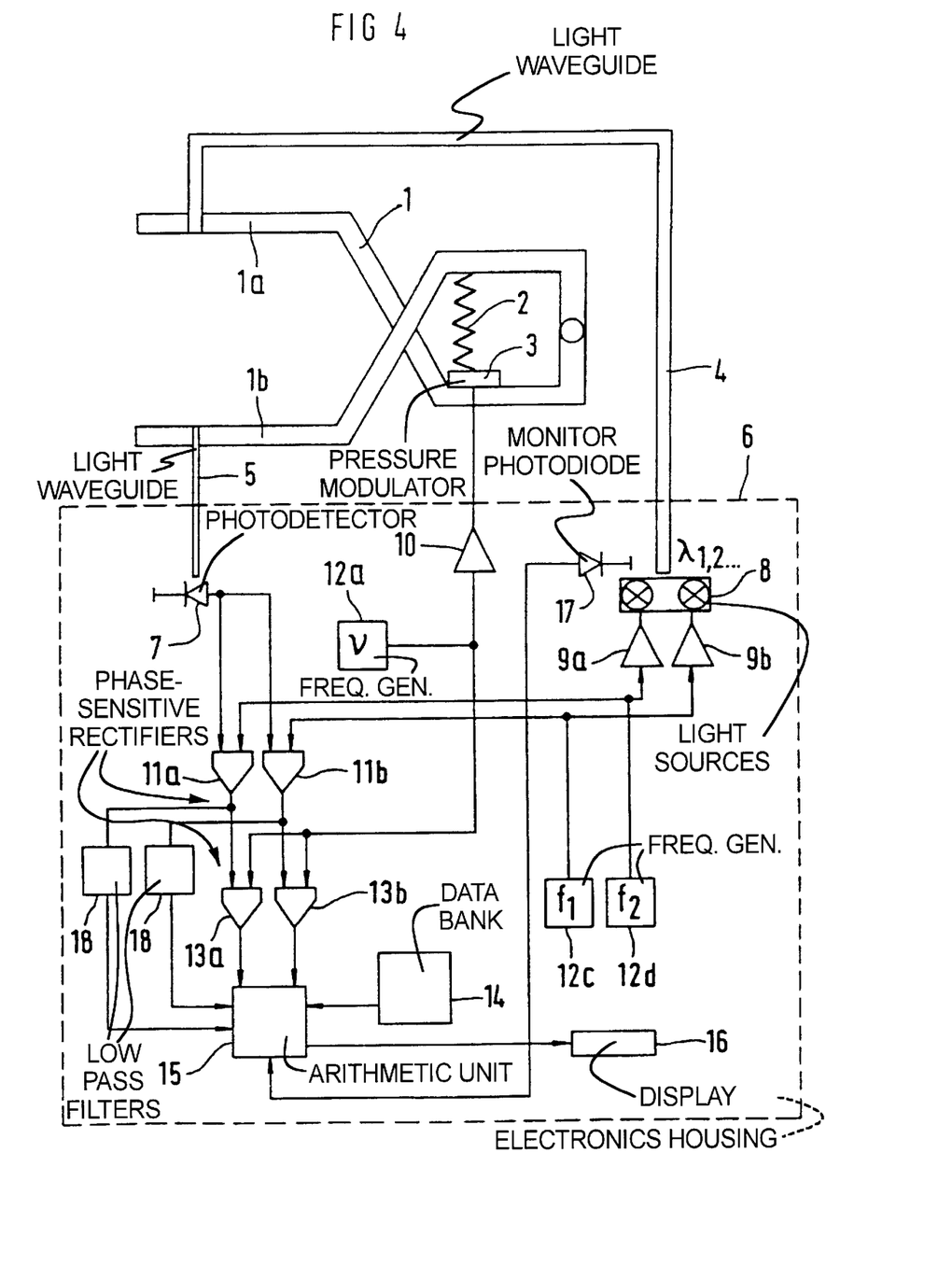
FIG. 4 is a schematic illustration of a modified version of the apparatus shown in FIG. 3, making use of reflection measurement.

The light signals reflected by the body part are measured given the exemplary embodiment shown in FIG. 4. To that end, the waveguide 5 has its light entry side ending in the inside jaw 1a of the clamp 1 next to the waveguide 4 that also ends thereat.

Figure 5:
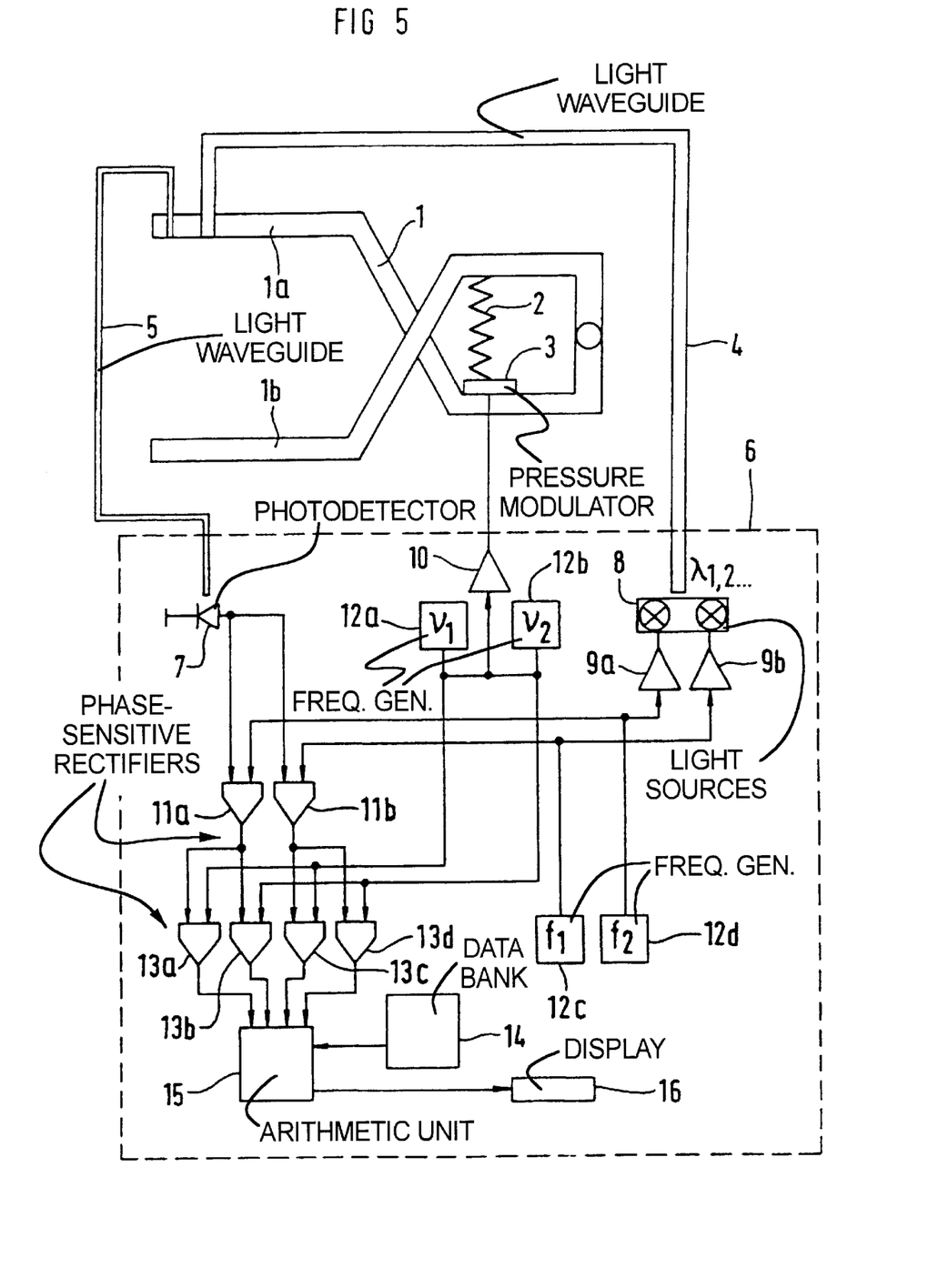
FIG. 5 is a schematic illustration of a further modification of the measuring apparatus shown in FIG. 3, wherein measurement is conducted opto-acoustically.

In the exemplary embodiment shown in FIG. 5, the absorption is measured via the opto-acoustic effect, whereby the light absorption in the tissue generates acoustic waves. A piezo-electric transducer 7a is arranged in the inside jaw 1a next to the light exit of the waveguide 4, this transducer 7a measuring the acoustic waves generated in the body part due to the absorption and converting them into electrical signals. The measured signals are edited via an amplifier 7b for the actual signal interpretation, this including amplification, filtering and rectification.

Figure 6:
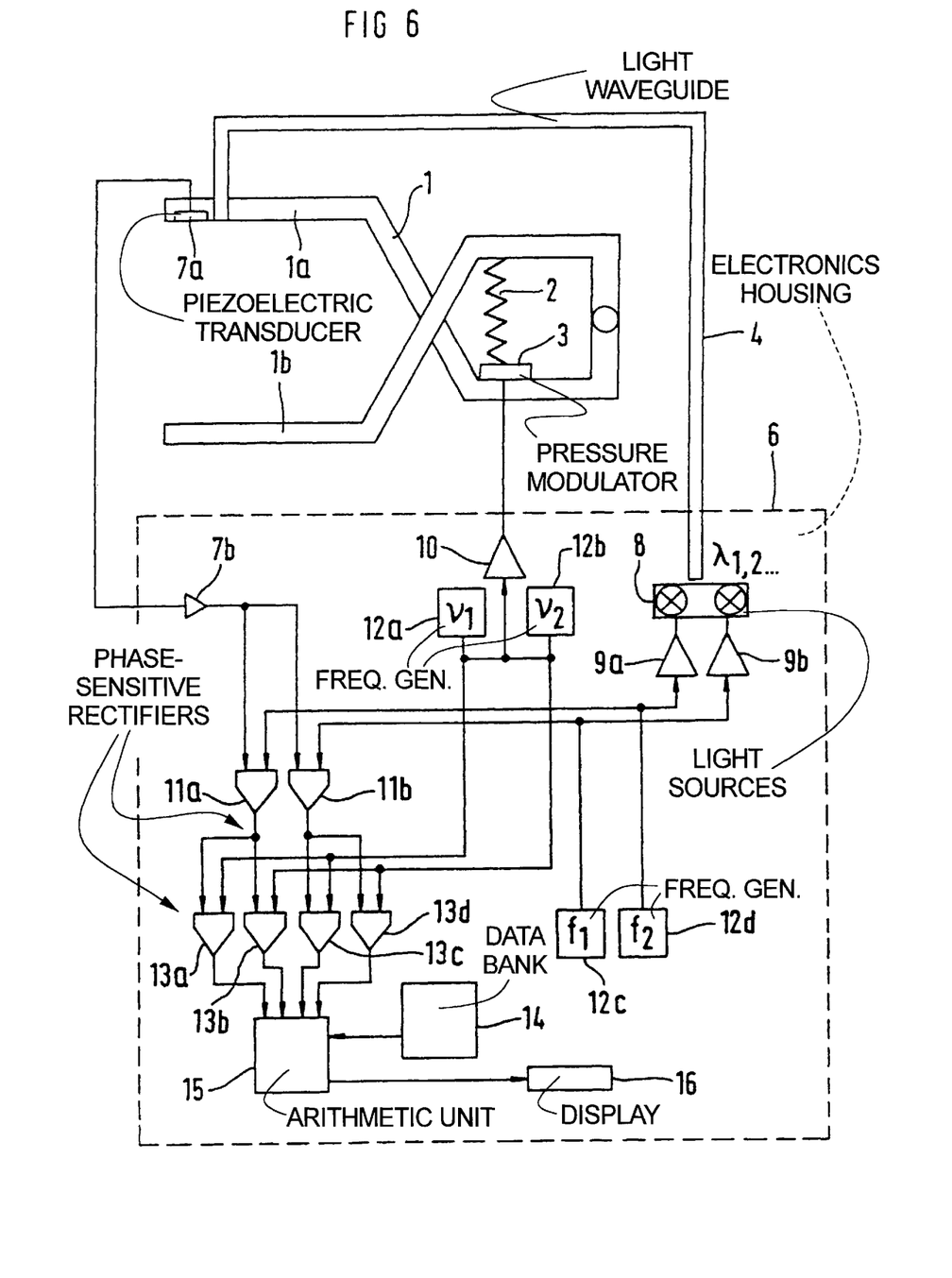
FIG. 6 schematically illustrates an exemplary embodiment for analog calculation of the concentration of the blood constituent in the method and apparatus of the invention.
Figure 7:
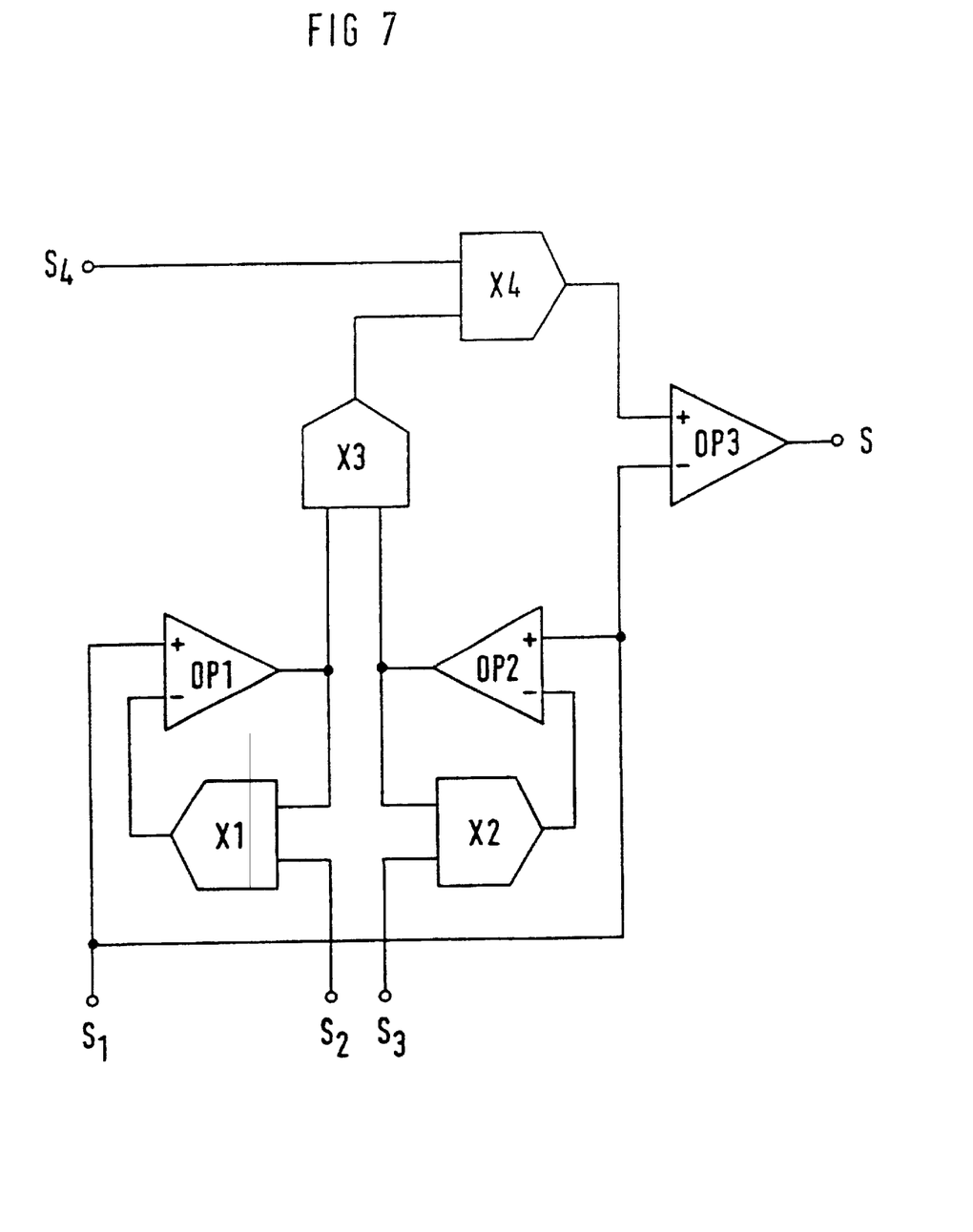
FIG. 7 illustrates an exemplary embodiment for the analog calculation of the concentration of the constituent.

FIG. 6 shows an exemplary embodiment for the analog calculation of the concentration of the signal S proportional to the consituent.

The analog multipliers X1 and X2 are connected as dividers with the assistance of the operational amplifiers OP1 and OP2; X1 and OP1 form the quotient $S_1/S_2$ from the input signals $S_1$ and $S_2$. Likewise, X2 and OP2 generate the quotient $S_1/S_3$ from the input signals $S_1$ and $S_3$. The two quotient signals are supplied to the multiplier X3 at whose output the product $S_1^2/(S_2S_3)$ is then available. This is multiplied by the input signal $S_4$ in the analog multiplier X4. The signal S proportional to the glucose concentration is ultimately acquired by forming the difference between the input signal $S_1$ and the generated signal $S_1^2 S_4/(S_2 S_3)$ in the operational amplifier OP3.

Analog multipliers having high stability and precision are currently available as standard components. The operational amplifiers required for operation as divider are already contained in these components.

As mentioned, it may be necessary for enhancing the measuring precision to employ more then two wavelengths $\lambda_1$, $\lambda_2$ and more then two pressure modulation frequencies $v_1$, $v_2$. When, thus, a total of n>2 signals $S_1 \ldots S_n$ are employed for calculating the constituent, it is more favorable to employ a digital arithmetic unit instead of an analog arithmetic unit, the digitalized signals $S_1 \ldots S_n$ being supplied thereto and this implementing the required calculating and correcting steps.

The application of the invention is not solely limited to the identification of the glucose concentration; rather, it can be expanded to other blood constituents such as cholesterol, albumin, urea, lactic acid and ethanol by selecting suitable wavelengths.

Although modifications and changes may be suggested by those skilled in the art, it is the intention of the inventors to embody within the patent warranted hereon all changes and modifications as reasonably and properly come within the scope of their contribution to the art.

We claim as our invention:

1. Method for non-invasive in vivo determination of a blood constituent in a body part by measuring the light absorption in the body part comprising the steps of harmonically modulating the body part in thickness with a pressure modulation frequency, and with a second pressure modulation frequency differing from zero and irradiating the thickness-modulated body part with light of at least two monochromatic wavelengths, at least one but not all of said wavelengths being lie in a range of optical absorption of the blood constituent, acquiring at least four measured signals that are dependent on an influence of the light as well as on a mechanical change in thickness, and determining a concentration of the blood constituent from the at least four measured signals.

2. Method according to claim 1, comprising simultaneously modulating the body part in thickness with the first and second pressure modulation frequencies.

3. Method according to claim 1 comprising simultaneously irradiating the body part with said light of at least two wavelengths and amplitude modulating the light of at least two wavelengths with respectively different frequencies.

4. Method according to claim 1 comprising acquiring the at least four measured signals after transmission through said body part with an optical detector.

5. Method according to claim 1 comprising acquiring the at least four measured signals after reflection by said body part with an optical detector.

6. Method according to claim 1 comprising acquiring the at least four measured signals with an acoustic detector.

7. Method according to claim 1 wherein the at least four measured signals have respectively different frequencies due to light modulation, and comprising separating said at least four measured signals by frequency filters according to the light modulation.

8. Method according to claim 7 comprising separating the frequencies of the light modulation.

9. Method according to claim 1 wherein the at least four measured signals have respectively different frequencies due to thickness modulation, and comprising separating said at least four measured signals by frequency filters according to the thickness modulation.

10. Method according to claim 9 comprising separating the frequencies of the thickness modulation by phase-sensitive rectifiers.

11. Method according to claim 1 wherein the first and second pressure modulation frequencies have different amplitudes.

12. Method according to claim 1 comprising selecting one of the pressure modulation frequencies so that only tissue is modulated but blood-filled vessels are not modulated.

13. Method according to claim 1 comprising synchronizing one of the pressure modulation frequencies with a heart beat.

14. Method according to claim 1 comprising forming a quantity from the at least four measured signals as a criterion for the concentration of the blood constituent, by forming a difference between a measured signal that arises at a first wavelength at which the blood constituent does not absorb and at the first pressure modulation frequency, and a product of a measured signal that arises at a second wavelength at which water and the blood constituent absorb and the second pressure modulation frequency, multiplied by a relationship of the at least four measured signals at the first wavelength and the first and second pressure modulation frequencies and the relationship of the at least four measured signals at the first and second wavelengths at the first pressure modulation frequency.

15. Method according to claim 1 comprising identifying glucose as said blood constituent.

16. Method according to claim 15, comprising comparing a quantity derived from the measured signals to results of a conventional blood glucose measurement and allocating said quantity to one of said results, and storing the allocation in a data bank.

17. An apparatus for non-invasive in vivo determination of blood constituents in a body part, comprising:

- a light source adapted to emit light into a body part;
- a detector disposed to detect light from said light source after passing through said body part;
- a compression unit adapted for placement on said body part for harmonically modulating said body part in thickness; and
- a first pressure modulation frequency generator, operating at a first pressure modulation frequency, and a second modulation frequency generator, operating at a second modulation frequency, connected to said compression unit, and said compression unit harmonically modulating said body part in thickness with said first and second pressure modulation frequencies.

18. An apparatus as claimed in claim 17 wherein said compression unit includes a piezoelectric transducer connected to said first and second pressure modulation frequency generators.

19. An apparatus as claimed in claim 17 wherein said compression unit includes a electromagnetic transducer connected to said first and second pressure modulation frequency generators.

20. An apparatus as claimed in claim 17 wherein said compression unit comprises a clamp having thermally insulated clamp jaws.

21. An apparatus as claimed in claim 17 wherein said compression unit comprises a clamp having thermostat-controlled clamp jaws.

* * * * *